United States Patent [19]
Rhenter

[11] Patent Number: 5,697,893
[45] Date of Patent: Dec. 16, 1997

[54] STRUCTURE FOR HOLDING THE ANKLE JOINT

[76] Inventor: Jean-Luc Rhenter, 25 Chemin des Greffières, 69450 Saint Cyr au Mont d'Or, France

[21] Appl. No.: 750,899

[22] PCT Filed: Jun. 14, 1995

[86] PCT No.: PCT/FR95/00780

§ 371 Date: Dec. 13, 1996

§ 102(e) Date: Dec. 13, 1996

[87] PCT Pub. No.: WO95/34257

PCT Pub. Date: Dec. 21, 1995

[30]  Foreign Application Priority Data

Jun. 14, 1994 [FR] France ................... 94 07503

[51] Int. Cl.⁶ .................................................. A61F 5/00
[52] U.S. Cl. ........................................ 602/27; 602/16
[58] Field of Search .............................. 602/5, 16, 23, 602/24, 27–29; 128/882

[56]  References Cited

U.S. PATENT DOCUMENTS 2,067,567  1/1937  Gruca .
2,832,334  4/1958  Whitelaw .
3,707,963  1/1973  Keropian .
4,489,718  12/1984  Martin .
4,697,583  10/1987  Mason et al. .
4,726,361  2/1988  Farley .
4,771,768  9/1988  Crispin .
5,000,169  3/1991  Swicegood et al. .
5,002,044  3/1991  Carter .
5,013,037  5/1991  Stermer .
5,025,801  6/1991  Callaway .
5,092,321  3/1992  Spademan .
5,103,807  4/1992  Makaran .

FOREIGN PATENT DOCUMENTS 8707498  12/1987  WIPO .
9302644  2/1993  WIPO .

Primary Examiner—Linda C. Dvorak
Attorney, Agent, or Firm—Harris Beach & Wilcox, LLP

[57]  ABSTRACT

A support structure for the ankle having three parts that are hinged together that include a rigid member that bears against the lower leg, a pedal shell that surrounds the planar arch and a sub astragalar shell that are brought together to provide a support for the ankle joint and can be used preventatively and curatively.

13 Claims, 5 Drawing Sheets

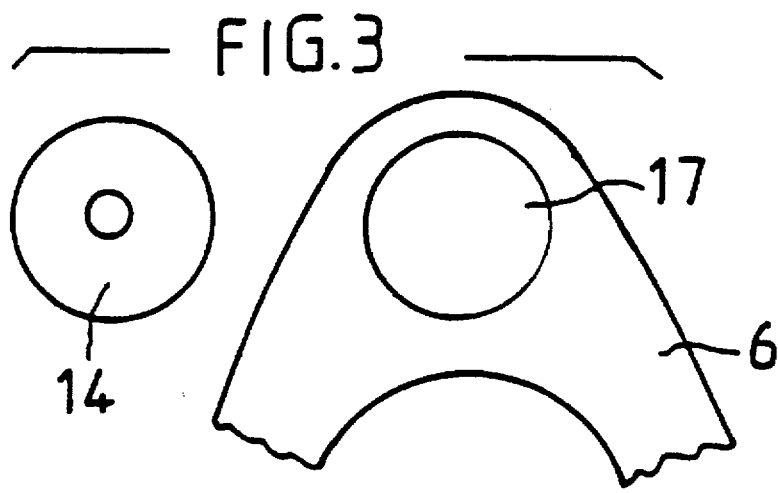
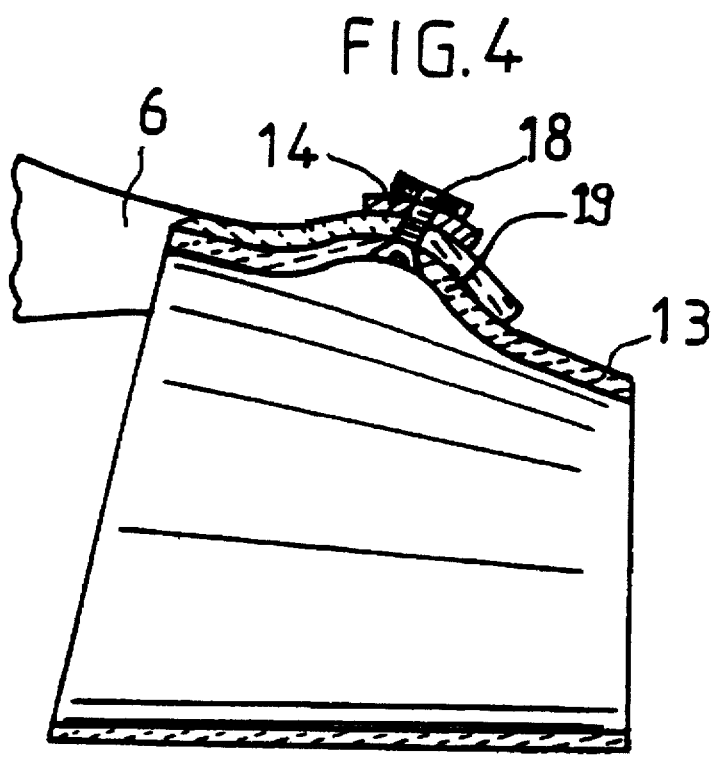

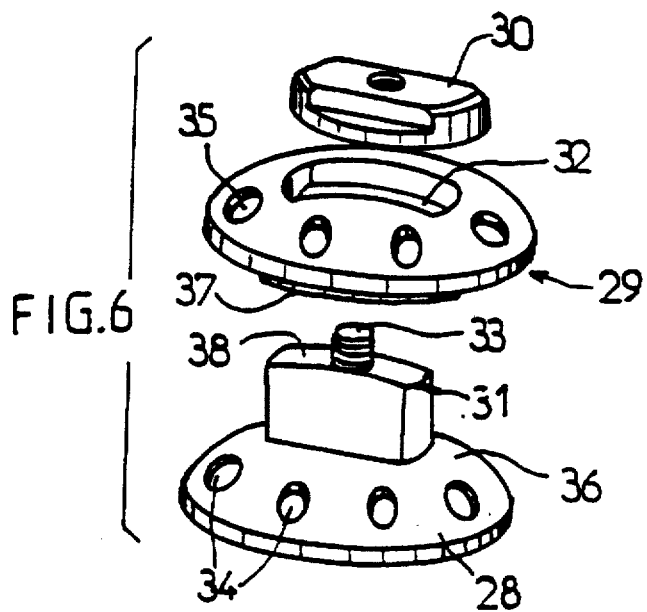
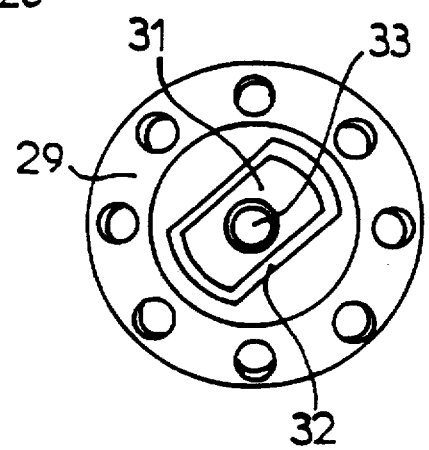
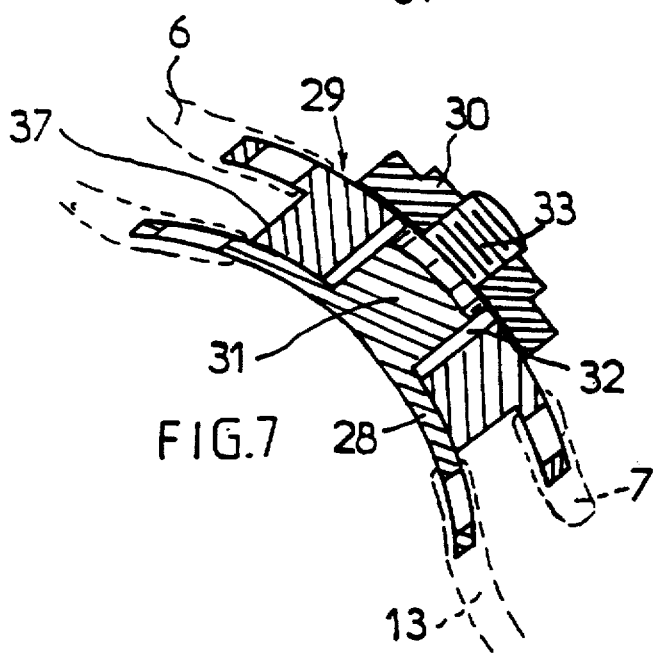

STRUCTURE FOR HOLDING THE ANKLE JOINT

BACKGROUND OF THE INVENTION

The invention relates to a support structure, more particularly one intended for the ankle joint. In the context of the invention, a support structure of this type can be used on its own, that is to say, it can be fitted independently of any shoe or boot, but may also be incorporated in a shoe or boot, in particular a sports shoe or boot.

The complexity of the movements which take place in the ankle joint makes it particularly susceptible to many types of trauma, so that efforts have long been made to support and hold this joint, in particular for preventive purposes. This is particularly appropriate when an activity, in particular a sporting activity, places great stresses on this joint.

Two categories of methods have to date been developed with a view to promoting support and holding of this joint for preventive purposes. The first consists in producing an ankle-length boot which includes rigid reinforcements. Although they leave the tibiotarsal articulation relatively free, boots of this type nevertheless somewhat restrict the freedom of movement inherent in the sub-astragalar articulation and furthermore affect the user's comfort at the very least.

Other shoes have also been proposed, which are less rigid and therefore more comfortable but in which the restraint produced at the ankle, both at the tibiotarsal articulation and the sub-astragalar articulation, is generally insufficient to support the ankle properly and does not make it possible to prevent trauma or limit trauma when it occurs.

Other, curative solutions are also known for treating sprained ankles and, more generally, ankle weaknesses. Further to the old method consisting in performing a surgical operation with a view to replacing or suturing the defective ligament or ligaments, which is time-consuming and painful, the use of elastic restraining straps, better known as strapping has also been proposed, which consists in tightly wrapping such a strap around the ankle joint. However, further to the fact that the ankle support which it provides is generally accepted to be insufficient, employing a strap of this type proves to be time-consuming and laborious before and after it is used. Finally, use is sometimes made of an ankle support consisting of a flexible and elastic fabric structure fitted like a stocking around the ankle, but this has the drawback that it supports the ankle only poorly.

SUMMARY OF THE INVENTION

The object of the invention is to provide a support structure for the ankle joint, which can be used preventively and curatively, which makes it possible to overcome these various drawbacks, it being possible for said structure to be used as an orthesis or to be incorporated directly in a shoe or ankle-length or other boot, in particular one for sport.

This structure is characterized in that it includes three parts which are articulated to one another, respectively:

- a rigid first part, referred to as the upper, intended to partially surround and bear against the lower end of the user's leg and subdivided in its end region into two branches which end at the said user's two malleoli;
- a second part, referred to as the pedal shell, intended to surround the foot at the plantar arch;
- and, finally, a third part, referred to as the connecting shell or sub-astragalar shell, which is substantially V-shaped and is intended to be articulated respectively, at the malleoli to the upper, at the two ends of the branches of the V, so as to allow displacement of said upper in the sagittal plane of the tibiotarsal articulation and, on the other hand, to the upper end of the pedal shell, at the tip of the V, so as to allow eversion and inversion movements of the pedal shell relative to the assembly consisting of the upper and the connecting shell.

In other words, the invention consists in producing a structure with three elements, articulated relative to one another, whose design allows them to to [sic] execute the different movements according to the natural degrees of freedom of the ankle joint, both relative to the sub-astragalar articulation and relative to the tibiotarsal articulation, while supporting said articulations so as to limit or even eliminate any risk of joint trauma in them, which the device and other shoes or boots known to date do not make it possible to achieve.

Indeed, although they to some extent hold the ankle joint, all these devices allow said joint to move only in the sagittal plane of the tibiotarsal articulation, while significantly or critically impairing the movement of the sub-astragalar articulation, that is to say the inversion and eversion movements of the foot.

According to an advantageous form of the invention, the articulation of the connecting shell to the pedal shell is positioned at a boss formed within the upper end of said pedal shell, on which boss a complementarily shaped region of the connecting shell interacts, which region is articulated by an articulation pin passing through the two shells, allowing said connecting shell to rotate relative to said pedal shell.

Furthermore, as a function of the extent of the throughhole formed in the connecting shell at the articulation region, the amplitude of the mutual relative displacement of said shells can be increased.

According to an advantageous characteristic of the invention, two inserts are incorporated, respectively in the pedal shell and the connecting shell at the region where they interact, said inserts being intended to interact with each other in order to allow eversion and inversion movements of the pedal shell relative to the upper/connecting shell assembly, as well as displacement of the upper by moving in the sagittal plane of the tibiotarsal articulation, the insert incorporated in said connecting shell having a through-hole which interacts, with some play, with a projection emerging from the insert incorporated in the pedal shell in order to allow proper relative movement of the elements constituting the support structure in these various degrees of freedom, this play being, however, limited by means of a locking nut which is screwed onto the threaded end of said projection.

BRIEF DESCRIPTION OF THE DRAWINGS

The way in which the invention may be embodied, and the advantages which result therefrom as well as the additional characteristics of the invention, will emerge more clearly from the following illustrative embodiment, given by way of indication and without implying any limitation with reference to the appended figures.

FIG. 3 is a detail view of the system for fixing and articulating the connecting shell to the pedal shell.

FIG. 4 is a sectional schematic representation of said articulation.

FIG. 6 is a schematic representation, in exploded perspective, of the member for connecting the pedal shell to the connecting shell, of which FIGS. 7 and 8 are respectively a sectional view and a plan view when said member is assembled.

DESCRIPTION OF THE INVENTION

Although described more particularly with reference to an ankle orthesis, and as already stated, the invention is not intended to be limited solely to this application and is fully suited to being incorporated, in particular, in a sports shoe or boot.

Figure 1:
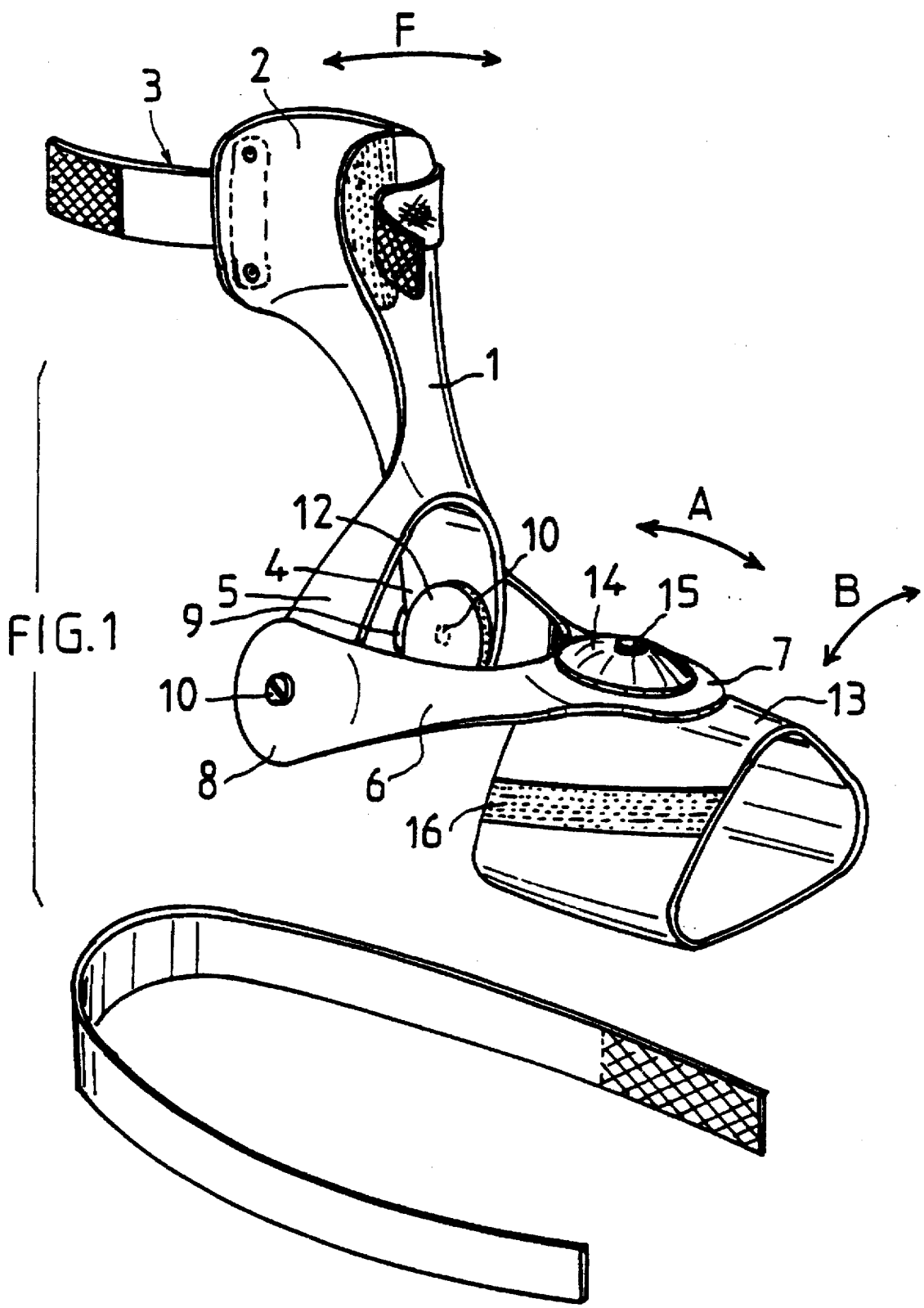
FIG. 1 is a schematic representation in perspective and side view of a structure for supporting the right foot according to the invention.

FIG. 1 represents a schematic lateral perspective view of this orthesis for a right foot. This orthesis or supporting structure has three basic elements, respectively:

a rigid upper (1);

a pedal shell (13);

a connecting shell (6), referred to as the sub-astragalar shell, articulated respectively to the lower end of the upper (1) and to the top of the pedal shell (13).

These various elements are made of a rigid material, for example carbon fibers, glass fibers, polyaramid fibers, or a mixture of carbon fibers with aramid fibers (Kevlar: registered trade mark), or even of thermoformable plastic. The latter material has the advantage of allowing production of a standard shell with the possibility of modifying the local morphology of one of these elements in order to adapt it partially to the user's foot.

With a view to obtaining improved comfort, all of the sub-astragalar shell (6) is made of a carbon-Kevlar mixture, in order to give it some flexibility compared to the rigidity of carbon fibers when used on their own, in particular in order to allow anatomical adaptation of said shell (6) for passage of the anterior leg tendon.

As can be seen in FIG. 1, the upper (1) partially encloses the lower end of the user's leg and ends at the lower region in two branches, the ends (4, 5) of which coincide substantially with the malleoli.

This upper (1) is reversibly fixed to the user's leg using an elastic strap (3) closed by interaction of a loop-hook system, according to the system well-known by the registered trade mark Velcro.

At the malleoli (10), this upper (1) is articulated to the sub-astragalar shell (6) by a slightly inclined articulation pin (11) corresponding substantially to the intermalleolar anatomical axis. In fact, the slightly inclined axis of the malleoli constitutes the first axis of articulation of the orthesis between the upper (1) and the sub-astragalar shell (6). In this way, the dynamic movement of the tibiotarsal articulation is reproduced exactly, according to the arrow F in FIG. 1.

In parallel, and with a view to optimizing the user's comfort, the inner face of the ends (4, 5) of the upper (1) accommodates a thin cushion (12) at the malleoli, for example a cushion made of polystyrene or neoprene which is intended to moderate the contact between the user's malleoli and the upper.

The sub-astragalar shell (6) substantially has the shape of a V, the end of whose two branches (8) and (9) respectively, are articulated to the malleoli to the outside of the upper (1). For its part, the tip (7) of the V is articulated at the pedal shell (13) and, more specifically, to its upper end.

According to a first embodiment of the invention, at the region where it is articulated to the sub-astragalar shell (6), the pedal shell (13) has a boss (19) (see FIG. 4) on which the end (7) of said sub-astragalar shell (6) interacts, which shell here has a corresponding shape in order to promote rotation of the end of the sub-astragalar shell at the pedal shell.

More specifically, the articulation pin (18) about which the sub-astragalar shell (6) can rotate pinches [sic] firstly an outer washer (14), of substantially circular shape, then the end of the sub-astragalar shell (6) and, finally, the boss (19) of the pedal shell (13).

In order to allow greater displacement of the sub-astragalar shell (6) when it rotates about and on the boss (19) of the pedal shell (13) (along arrows A and B in FIG. 1), the orifice which it includes in order to allow passage of the articulation pin (18) is converted into a through-hole (17), but the diameter of which remains, however, less than the diameter of the washer (14). It can be seen that, in this way, the possible rotational displacement of the sub-astragalar shell and of the upper which is directly articulated to it, relative to the pedal shell, can be increased at leisure. It is thus possible, advantageously and simply, to vary the degree of eversion and inversion displacement of the upper/sub-astragalar shell assembly relative to the pedal shell, and thereby of the ankle joint, by altering the dimensions of this hole (17).

In a particular embodiment of the invention, an intermediate element, with a shape corresponding to the shape of the boss (19) of the pedal shell (13), may advantageously be snap-fastened into the hole (17), in order to reduce the diameter of said hole (17) so as to limit the amplitude of the degrees of freedom of said sub-astragalar shell to rotate relative to the pedal shell.

According to another characteristic of the invention, the pin (18) for articulating the sub-astragalar shell (6) relative to the pedal shell (13) is oriented substantially along the sub-astragalar cone (26) defined below, and more specifically along the generatrix (27) of said sub-astragalar cone. Nevertheless, a tolerance of plus or minus 20° is accepted in the orientation of this pin in the sagittal plane of the tibiotarsal articulation relative to the reference constituted by the generatrix (27) of this sub-astragalar cone.

A definition of the meaning of the sub-astragalar cone will be given below, with the aid of FIG. 5 which represents a schematic lateral view of the ankle bone.

As is known, the lower end of the tibia (21) rests on the astragalus (22) which itself rests on the calcaneus (23) or heel bone. Up from the astragalus and the calcaneus, there are different bones, in particular the cuboid (24) and metatarsal (25) bones.

The astragalus and the calcaneus are intimately connected by means of ligaments which allow movements of the sub-astragalar articulation in an inversion movement and an eversion movement of the ankle. As is known, inversion of the ankle corresponds to a movement involving a combination of movements in the three space planes:

respectively in the horizontal plane, with internal rotation directed toward the inner face of the opposite foot, the maximum amplitude of which rotation is of the order of 30° relative to a standing position corresponding to alignment of the longitudinal axis of the foot with a plane parallel to the plane of symmetry of the human body, in the frontal plane, an internal roll movement with a maximum amplitude of about 25°, and, in the sagittal plane, so-called plantar flexion with an amplitude of about 10°.

Similarly, eversion of the ankle defines a set of three movements involving, in the three space planes, external rotation of maximum amplitude 30° in the horizontal plane, external rolling in the frontal plane and so-called dorsal flexion in the sagittal plane with an amplitude of about 10°.

Figure 5:
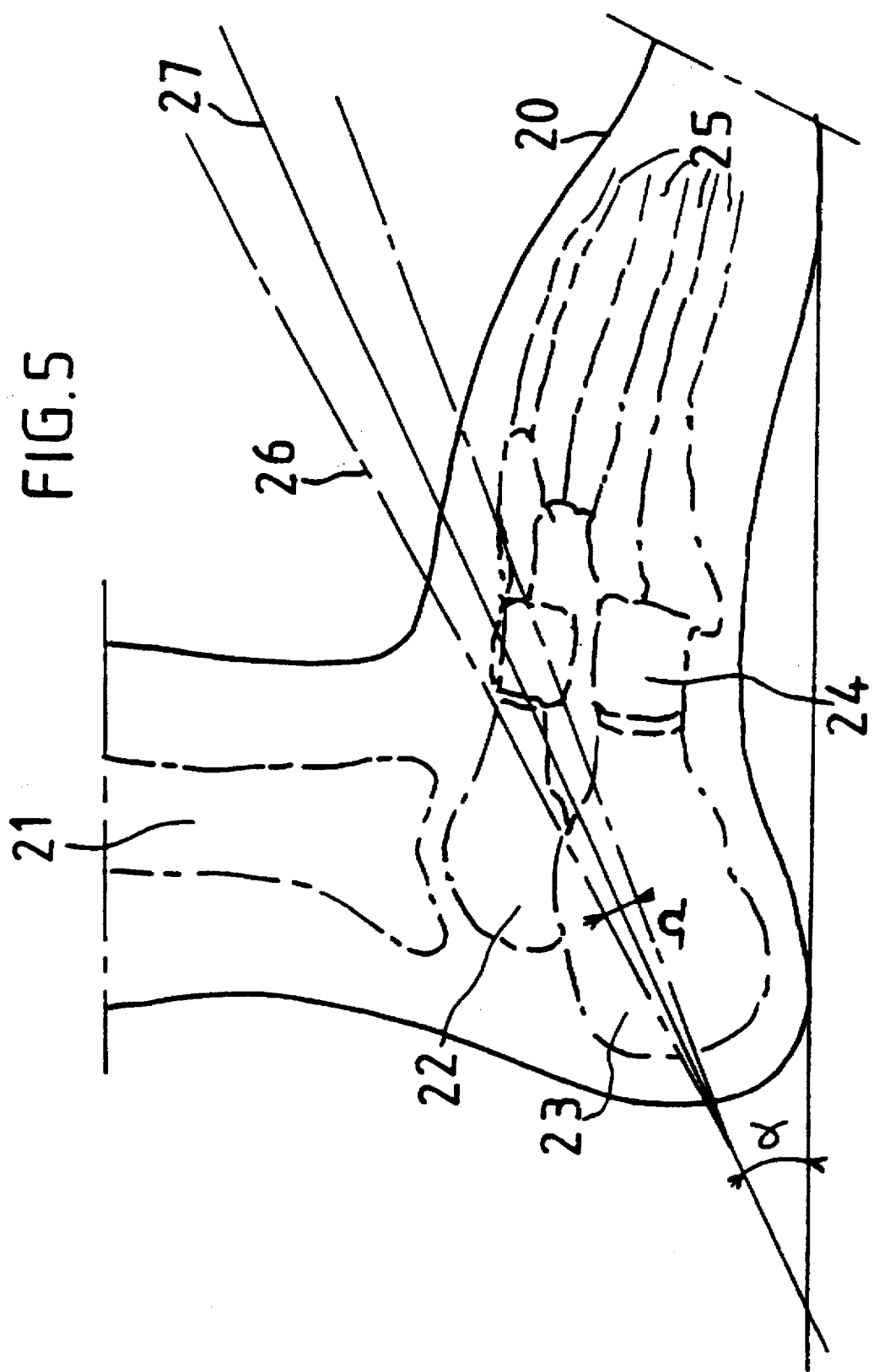
FIG. 5 is an external lateral schematic representation of the ankle joint.

The various anatomical studies carried out, in particular by the Applicant, have made it possible to show that the displacements and movements of the sub-astragalar articulation, in particular, and inversion and eversion movements are limited and are circumscribed by a geometrical envelope similar to a cone of revolution (26), referred to as the sub-astragalar cone, the vertex S of which lies substantially at one third of the height of the calcaneus and to its rear, as represented in FIG. 5. The generatrix (27) of the cone (26) has an inclination $\alpha$ relative to the horizontal plane on which the foot rests, the value of which is between 20° and 50°.

Finally, the cone (26) is defined by its aperture angle or vertex angle $\Omega$, the average value of which varies between 15° and 30° depending on the age of the individuals and their anatomical details.

According to another embodiment of the invention, described more particularly with reference to FIGS. 6 to 8, the sub-astragalar shell (6) is still articulated to the pedal shell (13) at the end (7) of said shell (6), but by means of inserts (28, 29), for example metal inserts, incorporated respectively in the pedal shell (13) and the sub-astragalar shell (6, 7). In fact, in order to facilitate this incorporation, said inserts (28, 29), which have a circular shape, are provided at their periphery with through-orifices (34, 35) intended to optimize the anchoring of the constituent materials of said shells when they are molded.

The insert (28) incorporated in the pedal shell (13) is domed and has symmetry of revolution, the convexity being directed outward, that is to say toward the top of the articulation. The axis of revolution of the insert is advantageously aligned with the generatrix (27) of the sub-astragalar cone (26) to within the tolerances already mentioned.

On its convex face (36), this insert (28) has a radial projection (31) oriented along the axis of revolution of the insert and extending symmetrically on either side of said axis. This projection (31) has a substantially rectangular cross section in which the two small sides are rounded. Finally, it is extended along the axis of revolution of the insert by a threaded rod (33) starting from its advantageously domed upper end (38).

The insert (29) incorporated in the end (7) of the sub-astragalar shell (6) also has a domed shape whose convexity is also directed toward the top of the articulation. Like the insert (28), it has symmetry of revolution, the axis of revolution of which is aligned with the generatrix (27) of the cone (26) to within tolerances.

This insert (29) has a base (37) with a smaller diameter than but with the same degree of convexity as the convex face (36) of the insert (28) on which it is intended to bear. Furthermore, the base (37) and the insert (29) are pierced by a through-hole (32) whose shape corresponds to the shape of the projection (31) of the insert (28) but whose dimensions are greater and are, for example, related to those of the projection (31) by homothetic ratios, as can be seen in FIG. 8.

The projection (31) is intended to interact with the hole (32) in the scope of articulating the sub-astragalar shell (6) to the pedal shell (13). In order to keep the two inserts (28, 29) tightly interacting, a nut (30) is screwed onto the threaded rod (33) extending the projection (31). Advantageously, this nut (30) has a concave lower face which can bear on the convex upper face (38) of the upper end of the projection (31), the length of the latter being slightly greater than the height of the hole (32) in order thus to make it possible to immobilize said nut in a position which can allow free displacement with different degress of freedom already mentioned of the insert (29) relative to the insert (28), and thereby of the sub-astragalar shell (6) relative to the pedal shell (13). Of course, the dimensions of the nut (30) are greater than those of the hole (32). In view of the particular shape of the hole (32) and of the projection (31), the orthesis can allow displacements according to the different degrees of freedom required.

Figure 2:
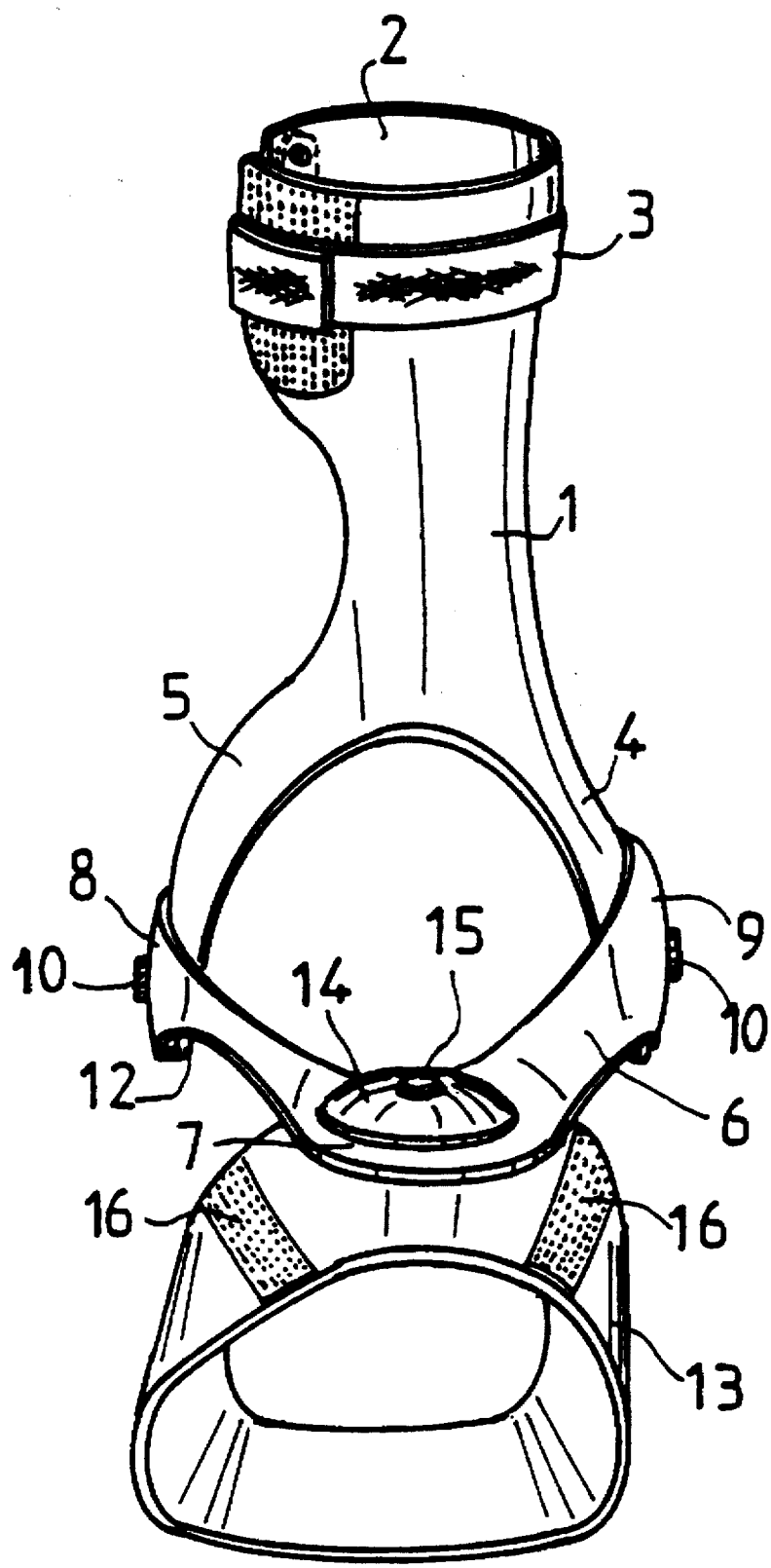
FIG. 2 is a perspective front view of the supporting structure in FIG. 1.

According to another characteristic of the invention, the orthesis is combined with a sock (not shown) made, for example, of neoprene which the user puts on before fitting the orthesis. This neoprene sock has a strap which passes around the heel and is intended to be fixed on the pedal shell (13) using a loop-hook system of the type well known by the registered trade mark Velcro, of which FIGS. 1 and 2 represent the complementary bands (16) intended to interact with said strap, in order to achieve coaptation of the calcaneus in the pedal shell. This sock may be replaced by an adhesively bonded foam lining.

In this way, fitting of the orthesis presupposes that the neoprene sock has been put on beforehand. The orthesis is then fixed while firstly taking great care to slide the foot fully into the bottom of the pedal shell (13), onto which the strap secured to the heel of the neoprene sock is then fitted as firmly as possible. Finally, the upper (1) is fixed on the leg, while tightening the strap which is associated with it.

This demonstrates the speed with which an orthesis of this type can be fitted, dramatically simplifying the procedures known hitherto, which moreover do not achieve efficient holding of the ankle and do not provide the possibility of displacement in all the anatomical degrees of freedom of this articulation.

In parallel, this fitting procedure is simplified if this orthesis is directly incorporated in a shoe or boot, in particular an ankle-length boot. This is because there is then no neoprene sock, coaptation of the foot in the pedal shell being ensured directly by the heel of the shoe or boot.

This orthesis has numerous advantages, and in particular the advantage that it keeps the two articulations, tibiotarsal and sub-astragalar respectively, supported while permitting or even slightly limiting the various movements of said articulations, with their natural anatomical degree of freedom. In parallel, by virtue of its design, a structure of this type can be fitted even with sports shoes or boots, or cross-country ski boots.

I claim:

1. A support structure for an ankle joint for preventative and curative use that includes
    a first rigid upper part arranged to partially surround and bear against the lower part of a user's leg, said upper part being bifurcated at its lower end to form two branches whereby the branches are locatable at the two malleoli of the user's ankle,
    a second pedal shell part being arranged to surround the user's foot at the plantar arch, and
    a third sub-astragalar shell part that is V-shaped having a body section and two arms that are pivotally attached to the branches of the first upper part to permit displacement of the first upper part in the sagittal plane of the tibiotarsal articulation, said body section being pivotally attached to said pedal shell part to permit eversion and inversion movement of the pedal shell relative to the first rigid part and the sub-astragalar shell part.

2. Support structure for the ankle joint according to claim 1, wherein the articulation of the sub-astragalar shell (6) to the pedal shell (13) is positioned at a boss (19) formed within the upper end of said pedal shell, on which boss a complementary shaped region of the sub-astragalar shell (6) interacts, which region is articulated by an articulation pin (18), passing through the two shells, allowing said shell (6) to rotate relative to said pedal shell (13).

3. Support structure for the ankle joint according to claim 2, wherein the region of the sub-astragalar shell (6) which co-operates with the articulation pin (18) and the boss (19) of the pedal shell (13) is pierced by a through-hole (17), the articulation furthermore including a washer (14), through which the articulation pin (18) also passes and which bears on said sub-astragalar shell (6) in order to hold said pin (18).

4. Support structure for the ankle joint according to claim 2, wherein the through-hole (17) formed in the sub-astragalar shell (6) can accommodate an intermediate element which has a shape corresponding to the shape of the boss (19) of the pedal shell (13) and is fixed reversibly on the periphery of said hole, by snap-fastening, so as to reduce the diameter of said hole (17) in order to limit the amplitude of the degrees of freedom of said sub-astragalar shell to rotate relative to the pedal shell.

5. Support structure for the ankle joint according to claim 2, wherein articulation pin (18) is oriented along the generatrix (27) of the sub-astragalar cone (26), the latter being defined as the geometrical envelope incorporating all the eversion and inversion movements of the ankle, with a tolerance of plus or minus 20° in the orientation of the pin (18) in the sagittal plane of the tibiotarsal articulation relative to the reference constituted by the generatrix (27) of said sub-astragalar cone (26).

6. Support structure for the ankle joint according to claim 1, wherein the sub-astragalar shell (6) is articulated to the pedal shell (13) by means of inserts (28, 29) incorporated in said shells (6, 13):

a first insert (28), which is incorporated in the pedal shell (13), is of domed shape, and has symmetry of revolution, the convexity being directed toward the top of said articulation, and has a radial projection (31) on its convex face (36), this projection being oriented along the axis of revolution of the insert and extending symmetrically on either side of said axis;

a second insert (29) which is incorporated in the end (7) of the sub-astragalar shell (6), is of domed shape, and has symmetry of revolution, the convexity being directed toward the top of the articulation, and has a base (37), with the same degree of convexity as the convex face (36) of the insert (28) on which it is intended to bear, the base (37) and the insert (29) being pierced by a through-hole (32) whose shape corresponds to the shape of the projection (31) of the insert (28) but has larger dimensions, the projection (31) of the insert (28) being intended to interact with said hole (32).

7. Support structure for the ankle joint according to claim 6, wherein the two inserts (28, 29) are kept in close interaction by means of a nut (30) whose dimensions are greater than those of the hole (32), said nut being screwed onto a threaded rod (33) extending from the projection (31).

8. Support structure for the ankle joint according to claim 7, wherein the nut (30) has a concave lower face which can bear on the convex upper face (38) of the upper end of the projection (31), the length of the latter being slightly greater than the height of the hole (32) in order to make it possible to immobilize said nut in a position which can allow free displacement of the insert (29) relative to the insert (28), and thereby of the sub-astragalar shell (6) relative to the pedal shell (13) in eversion and inversion movements as well as in the sagittal plane of the tibiotarsal articulation.

9. Support structure for the ankle joint according to claim 6, wherein the axes of revolution of the inserts (28, 29) are aligned with the generatrix (27) of the sub-astragalar cone (26), the latter being defined as the geometrical envelope incorporating all the eversion and inversion movements of the ankle, with a tolerance of plus or minus 20° in the orientation of said axes in the sagittal plane of the tibiotarsal articulation relative to the reference constituted by the generatrix (27) of said sub-astragalar cone (26).

10. Support structure for the ankle joint according to claim 6, wherein the projection (31) and the through-hole (32) are of substantially rectangular shape, in which the two small sides are rounded, and in that the dimensions of the projection (31) and of the through-hole (32) are related to one another by homothetic ratios.

11. Support structure for the ankle joint according to claim 1, wherein it furthermore comprises a sock, made of neoprene, intended for the user to put on before said structure is fitted, said sock being provided with a strap which is secured in the posterior region and is intended to be fixed reversibly on the top of the pedal shell (13) in order to induce coaptation of the user's foot within said pedal shell.

12. Support structure for the ankle joint according to claim 1, wherein it is incorporated in a shoe or boot, coaptation of the user's boot within the pedal shell (13) then being induced directly by the heel of the shoe or boot.

13. Support structure for the ankle joint according to claim 1, wherein it is made of a material chosen from the group comprising carbon fibers, glass fibers, polyaramid fibers or a mixture thereof, and thermoformable plastics.

* * * * *